US010405504B2

(12) United States Patent
Chan et al.

(10) Patent No.: US 10,405,504 B2
(45) Date of Patent: Sep. 10, 2019

(54) ACTIVE SUBSTANCES FOR PREVENTING HEARING DETERIORATION, THE COMPOSITION CONTAINING THE ACTIVE SUBSTANCES, AND THE PREPARATION METHOD THEREOF

(71) Applicant: GRAPE KING BIO LTD., Taoyung (TW)

(72) Inventors: Yin-Ching Chan, Taoyuan (TW); Chin-Chu Chen, Taoyuan (TW); Li-Ya Lee, Taoyuan (TW); Wan-Ping Chen, Taoyuan (TW)

(73) Assignee: GRAPE KING BIO LTD., Taoyuan (TW)

( * ) Notice: Subject to any disclaimer, the term of this patent is extended or adjusted under 35 U.S.C. 154(b) by 0 days.

(21) Appl. No.: 15/545,087

(22) PCT Filed: Jan. 4, 2016

(86) PCT No.: PCT/CN2016/070019
§ 371 (c)(1),
(2) Date: Jul. 20, 2017

(87) PCT Pub. No.: WO2017/117701
PCT Pub. Date: Jul. 13, 2017

(65) Prior Publication Data
US 2018/0007836 A1    Jan. 11, 2018

(51) Int. Cl.
| *A01N 63/00* | (2006.01) |
| *A01G 18/00* | (2018.01) |
| *A61K 36/07* | (2006.01) |
| *C12M 1/00* | (2006.01) |
| *C12M 1/12* | (2006.01) |
| *C12M 1/42* | (2006.01) |
| *C12N 1/14* | (2006.01) |
| *C12N 5/00* | (2006.01) |

(52) U.S. Cl.
CPC .............. *A01G 18/00* (2018.02); *A61K 36/07* (2013.01); *C12M 1/005* (2013.01); *C12M 25/06* (2013.01); *C12M 35/04* (2013.01); *C12N 1/14* (2013.01); *C12N 5/0025* (2013.01); *A61K 2236/11* (2013.01); *C12N 2533/76* (2013.01)

(58) Field of Classification Search
CPC ..................................................... A01G 18/00
See application file for complete search history.

(56) References Cited

U.S. PATENT DOCUMENTS 5,556,754 A * 9/1996 Singer .................... A61K 31/00
435/6.16

FOREIGN PATENT DOCUMENTS

| CN | 101971762 A | 2/2011 |
| CN | 102835251 A | 12/2012 |
| CN | 103664318 A | 3/2014 |
| CN | 104543997 A | 4/2015 |
| CN | 104939061 | * 9/2015 |
| KR | 20130029294 A | 3/2013 |
| TW | 201600021 A | 1/2016 |

OTHER PUBLICATIONS

He et al (International Conference on Logistics Engineering, Management and Computer Science, pp. 211-220) (Year: 2015).*
Gates et al (Lancet vol. 366, pp. 1111-1120) (Year: 2005).*
Schuknecht, H. F. and Gacek, M. R. Cochlear pathology in presbycusis. Ann. Otol. Rhinol. Laryngol. 1993. 102 (1 Pt 2): 1-16.
Mao, X.-L., "Chinese Edible and Pharmaceutical Large Fungi", Microbiology China, 1989, 16(5): 290-297.
Wang, J.C., Hu, S.H., Su, C.H. and Lee, T.M. Antitumor and immunoenhancing activities of polysaccharide from culture broth of *Hericium* spp. Kaohsiung J. Med. Sci. 2001. 17(9): 461-467.
Yang, B.-K., Park, J.-B. and Song, C.-H. Hypolipidemic effect of an Exo-biopolymer produced from a submerged mycelial culture of *Hericium erinaceus*. Biosci. Biotechnol. Biochem. 2003. 67(6): 1292-1298.
Saito T., A F., Hirai H., Inagaki, T., Matsunaga, Y., Sakakibara, T., Sakemi, S., Suzuki, Y., Watanabe, S., Suga, O., Sujaku, T., Smogowicz, A.A., Truesdell, S.J., Wong, J.W., Nagahisa, A., Kojima, Y. and Kojima, N. Erinacine E as a kappa opioid receptor agonist and its new analogs from a basidiomycete, Hericium ramosum. J. Antibiot. 1998. 51(11): 983-990.
Kenmoku, H., Shimai, T., Toyomasu, T., Kato, N. and Sassa, T. Erinacine Q, a new erinacine from Hericium erinaceum, and its biosynthetic route to erinacine C in the basidiomycete. Biosci. Biotechnol. Biochem. 2002. 66(3): 571-575.
Kenmoku, H., Tanaka, K., Okada, K., Kato, N. and Sassa, T. Erinacol (cyatha-3,12-dien-14β-ol) and 11-O-acetylcyathin A3, new cyathane metabolites from an erinacine Q-producing Hericium erinaceum. Biosci. Biotechnol. Biochem. 2004. 68(8): 1786-1789.
Watanabe, H., Takano, M., Umino, A., Ito, T., Ishikawa, H. and Nakada, M. Enantioselective total synthesis of (−)-erinacine B. Org. Lett. 2007. 9(2): 359-362.
Watanabe, H. and Nakada, M. Biomimetic Total Synthesis of (−)-Erinacine E. J. Am. Chem. Soc. 2008. 130(4): 1150-1151.
Lee, K.-F., Chen, J.-H., Teng, C.-C., Shen, C.-H., Hsieh, M.-C., Lu, C.-C., Lee, K.-C., Lee, L.-Y., Chen, W.-P., Chen, C.-C., Huang, W.-S. and Kuo, H.-C. Protective effects of Hericium erinaceus mycelium and its isolated erinacine A against ischemia-injury-induced neuronal cell death via the inhibition of iNOS/p38 MAPK and nitrotyrosine. Int. J. Mol. Sci. 2014. 15(9): 15073-15089.

(Continued)

*Primary Examiner* — Albert M Navarro
(74) *Attorney, Agent, or Firm* — Volpe and Koenig, P.C.

(57) ABSTRACT

The present invention discloses the active substances for preventing hearing deterioration, its preparation method, the pharmaceutical composition containing the active substances, and the preparation method of the pharmaceutical composition. The preparation method of the active substances is performed by plate cultivation, flask cultivation and fermentation tank cultivation, to obtain the active substances of *Hericium erinaceus* mycelia in powder form. The powder of *H. erinaceus* mycelia is proved to have the effect of preventing hearing deterioration.

2 Claims, 1 Drawing Sheet

(56) References Cited

OTHER PUBLICATIONS

Li, I.-C., Chen, Y.-L., Lee, L.-Y., Chen, W.-P., Tsai, Y.-T., Chen, C.-C. and Chen, C.-S. Evaluation of the toxicological safety of erinacine A-enriched Hericium erinaceus in a 28-day oral feeding study in Sprague-Dawley rats. Food Chem. Toxicol. 2014. 70: 61-67.

Nagai, K., Chiba, A., Nishino, T., Kubota, T. and Kawagishi, H. Dilinoleoyl-phosphatidylethanolamine from Hericium erinaceum protects against ER stress-dependent Neuro2a cell death via protein kinase C pathway. J. Nutr. Biochem. 2006. 17(8): 525-530.

Jia, L.-M., Liu, L., Dong, Q., Fang, J.-N. Structural investigation of a novel rhamnoglucogalactan isolated from the fruiting bodies of the fungus Hericium erinaceus. Carbohydr. Res. 2004. 339(16): 2667-2671.

Starr, A. and Achor, L. J. Auditory brain stem responses in neurological disease. Arch. Neurol. 1975. 32(11): 761-768.

Butterfield, D. A. and Poon, H. F. The senescence-accelerated prone mouse (SAMP8): a model of age-related cognitive decline with relevance to alterations of the gene expression and protein abnormalities in Alzheimer's disease. Exp. Gerontol. 2005. 40(10): 774-783.

Yu Wang, et al., Optimization of fermentation medium for improving mycelium of Hencium erinaceus (Bull.) Per. Northern Horticulture, 2011(09): 202-204.

Chu, Jie, "Balancing Diet to Prevent Senile Deafness (or Regulating Diet to Prevent Presbycusis)", Food and Health, No. 11, 1998, p. 23.

\* cited by examiner

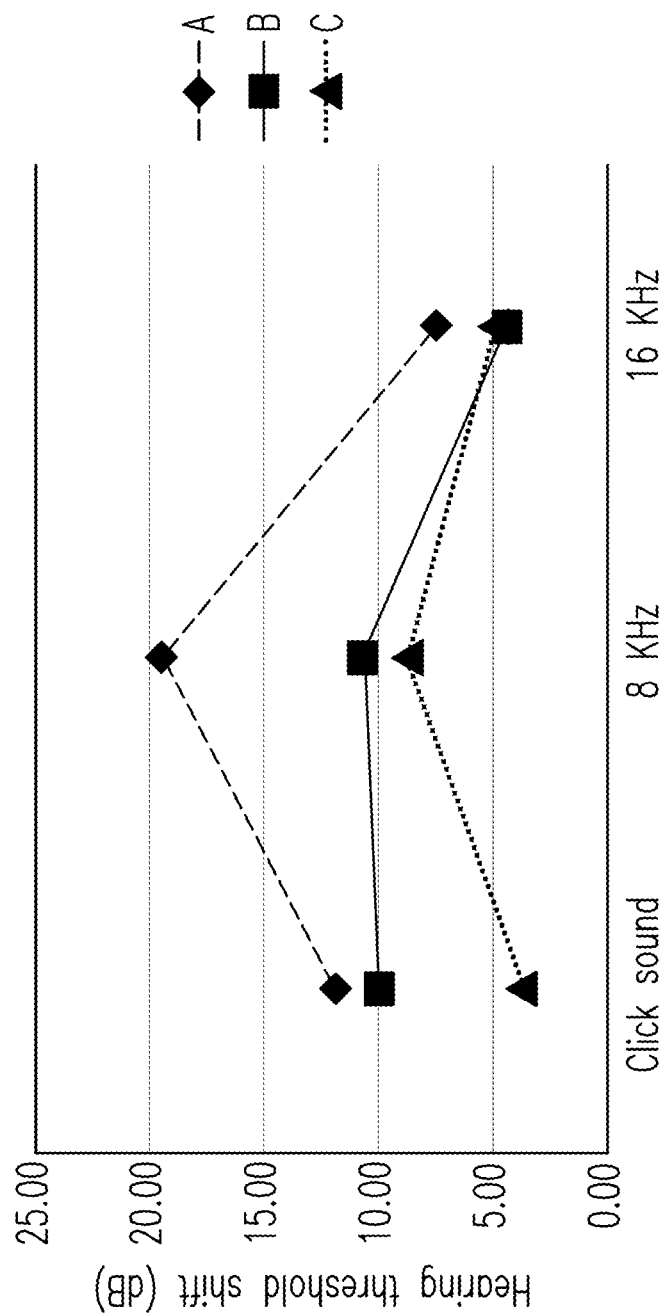

ACTIVE SUBSTANCES FOR PREVENTING HEARING DETERIORATION, THE COMPOSITION CONTAINING THE ACTIVE SUBSTANCES, AND THE PREPARATION METHOD THEREOF

CROSS REFERENCE TO RELATED APPLICATIONS

This application is a 35 USC § 371 national stage application of PCT/CN2016/070019, which was filed Jan. 4, 2016 and is incorporated herein by reference as if fully set forth.

FIELD OF THE INVENTION

The present invention is related to an active substance for preventing hearing deterioration, its preparation method, a pharmaceutical composition containing the active substance, and the preparation method of the pharmaceutical composition, in particular, a pharmaceutical composition containing the active substance of *Hericium erinaceus* mycelia and its preparation method.

BACKGROUND OF THE INVENTION

Presbycusis

The morbidity rate for various degeneration diseases increases along with human longevity. The common degeneration diseases are the degeneration of bones and sensory functions, wherein the degeneration of auditory functions is one of the most common sensory degeneration diseases in the elderly.

Presbycusis is also named as age-related hearing loss (ARHL), which means that the level of hearing deterioration of the two ears worsens as patients get older. Basically, ARHL is further divided into neural hearing loss and sensory hearing loss, wherein neural hearing loss is caused by auditory (acoustic) nerve deterioration, and sensory hearing loss is caused by cochlear deterioration. However, both losses are clinically difficult to distinguish from each other. Thus, both losses are collectively nominated as sensorineural hearing loss. The main causes of the hearing loss are considered as senescence, oxidation damage, mitochondrial damage or environmental pressure. This hearing damage usually is prevalent in people more than 50 years old, and the earliest symptom is hearing loss at high frequencies. That is, compared to the vowels in a language, it is increasingly difficult to hear consonants (the high-frequency portion of a language). The symptoms mentioned above are particularly significant in a noisy environment. A patient's central nervous system will slow down the processing rate of the auditory messages, so that the patients need to spend more time to decode the received auditory messages. Clinically, the pathological characteristics of the disease are an increased hearing threshold shift and decreased speech comprehension. These symptoms affect the patients' capacity for voice reception and language recognition, causing a significant communication disability, that affects socializing, expressing emotions, and the quality of life.

According to the pathological sites for presbycusis, H. F. Schuknecht divided presbycusis into four types in the report "*Cochlear pathology in presbycusis*" (Schuknecht, H. F. and Gacek, M. R. Cochlear pathology in presbycusis. Ann. Otol. Rhinol. Laryngol. 1993. 102 (1 Pt 2): 1-16):

1. Sensory presbycusis: The numbers of sensory cells and supporting cells in the corti become fewer or their functions deteriorate.

2. Neural presbycusis: This is caused by the decreased number of spiral ganglion cells or the neuronal degeneration, thereby affecting the transmission of hearing messages.

3. Metabolic/strial presbycusis: The degeneration and atrophy of the stria vascularis result in insufficient bloodstream for transporting nutrients.

4. Mechanical/cochlear presbycusis: This is caused by basement membrane degeneration, including the thickened width, the reduced elasticity or the hardening (due to calcification) of the basement membrane.

*Hericium erinaceus*

According to the description in *Medicinal Fungi of China*, "*H. erinaceus* tastes sweet, is neutral and tonic, has benefits for five viscera and digestion, and has excellent effects on dyspepsia, neurodegeneration, duodenal ulcers and gastric ulcers" (Mao, X.-L. Chinese edible and pharmaceutical large fungi. Microbiology China, 1989. 16(5):290-297). Therefore, it is known that *H. erinaceus*, a pharmaceutical and edible fungus, has a history of disease treatment in ancient medicine. *H. erinaceus* is classified in the kingdom Fungi, the phylum Eumycota, the subphylum Basidiomycotina, the class Basidiomycetes, the order Aphyllophorales, the family Hydnaceae, the subfamily Hericioideae, and the genus *Hericium*. *H. erinaceus*'s fruiting body has a soft and spherical appearance with long rough protuberances. *H. erinaceus* is white when fresh and turns tawny after being dried. The *H. erinaceus* fruiting body or mycelia extract contains saccharides (Wang et al., Kaohsiung J. Med. Sci., 2001, 17(9):461-467; Yang et al., Biosci. Biotechnol. Biochem., 2003, 67(6):1292-1298), erinacines (Saito et al., J. Antibiot., 1998, 51(11):983-990; Kenmoku et al., Biosci. Biotechnol. Biochem., 2002, 66(3):571-575; Kenmoku et al., Biosci. Biotechnol. Biochem., 2004, 68(8):1786-1789; Watanabe et al., Org. Lett., 2007, 9(2):359-362; Watanabe and Nakada, J. Am. Chem. Soc., 2008, 130(4):1150-1151; Lee et al., Int. J. Mol. Sci., 2014, 15(9):15073-15089; Li et al., Food Chem. Toxicol., 2014, 70:61-67), dilinoleoyl-phosphatidylethanolamine (DLPE) (Nagai et al., J. Nutr. Biochem., 2006, 17(8):525-530), amino acids, proteins, and minor elements (Jia et al., Carbohydr. Res., 2004, 339(16): 2667-2671). In the literature, it is common knowledge that polysaccharides of *H. erinaceus* have effects on immunoregulation, blood lipid reduction, blood sugar reduction, gastric inflammation inhibition, or stomach cancer prevention. However, there have been no literature showing that *H. erinaceus* has the effect of preventing hearing deterioration.

SUMMARY OF THE INVENTION

The purpose of the present invention is to disclose a preparation method for an active substance of *H. erinaceus*, and the preparation method is used to prepare the active substance for preventing hearing deterioration.

To achieve the purpose above, the preparation method for the active substance of *H. erinaceus* disclosed in the present invention includes the following steps:

(a) inoculating the mycelium of *H. erinaceus* on an agar plate to be incubated at a temperature of 15-32° C. for 8-16 days;

(b) inoculating the incubated mycelium of *H. erinaceus* from step (a) into a medium in a flask to be incubated at a temperature of 20-30° C. and pH 4.5-6.5 for 3-5 days;

(c) inoculating the incubated mycelium of *H. erinaceus* from step (b) into a medium in a fermentation tank to be incubated at a temperature of 24-32° C. and pH 4.5-5.5 for 8-16 days to obtain a fermented medium of the mycelium of *H. erinaceus*; and (d) desiccating the fermented medium of the mycelium of *H. erinaceus* from step (c) to obtain a powder of the mycelium of *H. erinaceus*.

Preferably, an incubation in step (b) is a shaking incubation at a shaking rate of 100-250 rounds per minute (rpm).

Preferably, in the preparation method above, the fermentation tank in step (c) has a tank pressure of 0.8-1.2 kg/cm2 and a stirring rate of 10-150 rpm, and a gas is introduced into the fermentation tank at an aeration rate of 0.5-1 volume per volume per minute (vvm).

Preferably, in the preparation method above, the gas is air, oxygen, carbon dioxide, nitrogen gas or a combination thereof.

Preferably, in the preparation method above, the medium used in step (b) and the medium used in step (c) are the same.

Preferably, in the preparation method above, the medium includes a complex carbon and nitrogen source, animal or plant sources of protein or a hydrolyzate thereof, an inorganic salt, a saccharide, a yeast or a malt extract, a defoaming agent or a combination thereof.

Preferably, in the preparation method above, the complex carbon and nitrogen source is a grain or a legume, and the inorganic salt is a sulfate or a phosphate.

In the present invention, an active substance of *H. erinaceus* for preventing the hearing deterioration is disclosed and prepared using the method above.

Preferably, when the active substance is prepared using the method above, the active substance of *H. erinaceus* is in the form of powder.

In the present invention, a pharmaceutical composition for preventing the hearing deterioration is disclosed and includes the active substance of *H. erinaceus* mycelium above, and a biologically acceptable carrier, excipient, diluent or adjuvant.

In the present invention, a method for preparing a pharmaceutical composition for preventing hearing deterioration is further disclosed and includes: mixing an effective amount of the active substance of *H. erinaceus* mycelium with the biologically acceptable carrier, excipient, diluent or adjuvant.

Preferably, the active substance of *H. erinaceus* mycelium includes an active substance above.

A use or an application is further disclosed in the present invention, wherein the pharmaceutical composition for preventing hearing deterioration includes the active substance of *H. erinaceus* mycelium. That is, the use or the application of the active substance of *H. erinaceus* mycelium mentioned above is used for preparing the pharmaceutical composition for preventing hearing deterioration.

BRIEF DESCRIPTION OF THE DRAWINGS

FIG. 1 illustrates the hearing threshold shifts before and after the feeding experiment in the Embodiment 5, wherein the experimental mice were fed with the *H. erinaceus* active substances-containing diet, and the hearing thresholds before and after the experiment are determined using the auditory brainstem response.

DETAILED DESCRIPTION OF THE PREFERRED EMBODIMENTS

The purpose of the present invention is to provide a pharmaceutical composition and its preparation method, the pharmaceutical composition obtained using the preparation method includes the active substances of *H. erinaceus* mycelia in powder form, and the pharmaceutical composition can achieve the purpose of preventing hearing deterioration.

Experimental Method

The Source of the Species:

The species, *Hericium erinaceus*, used in the embodiments of the present invention was purchased from the Bioresource Collection and Research Center (BCRC) of the Food Industry Research and Development Institute, Taiwan, with the Accession No. BCRC 35669. However, the active substances of *H. erinaceus* described in the present invention are not limited to the one obtained from this species.

Submerged Cultivation:

The liquid culture of the *H. erinaceus* mycelia is described as follows. The mycelium of *H. erinaceus* was inoculated on an agar plate to incubate at an adequate temperature of 15-32° C. for about 14 days. Subsequently, the mycelium was inoculated into a medium (where the ingredients are listed below) in a flask, and incubated to the early log phase with shakes at 20-30° C., pH 4.5-6.5 at the shaking rate of 100-250 rounds per minute (rpm) for 3-5 days. Finally, the culture in the flask was inoculated into the medium (which has the same ingredients as in the flask) of the fermentation tank, and cultured at 24-32° C., a tank pressure of 0.8-1.2 kg/cm$^2$, a pH value of about 4.5-5.5, an aeration rate of a gas of 0.5-1 volume per volume per minute (vvm) and a stirring rate of 10-150 rpm for 8-16 days to obtain a fermentation medium of *H. erinaceus* mycelia including the mycelia and the supernatant, where the gas is air, a mixture of air, oxygen, carbon dioxide or nitrogen, and the preferred gas is air.

The formula of the medium is listed as follows.

| Ingredients | Amount (wt. %) |
| --- | --- |
| Complex carbon and nitrogen source | 0.01-10 |
| Animal or plant sources of protein or its hydrolyzate | 0.01-5 |
| Yeast or malt extract thereof (powder or cream) | 0.001-2 |
| Inorganic salt | 0.0001-2 |
| Saccharide | 0.01-20 |
| Defoaming agent | 0.01-0.5 |
| Water | Add to 100 wt. % |

The complex carbon and nitrogen source may be grain (e.g. wheat powder or wheat bran) or legume (e.g. soybean flour, mung bean flour and so on), the inorganic salt may be magnesium sulfate, potassium hydrogen phosphate, potassium dihydrogen phosphate, ferric sulfate, zinc sulfate and so on, the saccharide may be glucose, fructose, maltose, sucrose and so on, and the remainder is water in addition to the ingredients above.

A defoaming agent may be additionally supplemented into the medium in the fermentation tank to prevent the generation of too much foam during the cultivation, and may be commercially common ones, such as a 0.01% water-based defoaming agent including silicon oil and silicones. The cultivation method in the embodiment is described below in detail.

The Preparation of the Active Substances

The fermentation medium obtained above was desiccated to obtain the active substances of *H. erinaceus* mycelia in powder form, and the desiccating method may be, for example, spray drying, hot-air drying, roller drying, freeze drying or other desiccating methods suitable for the present invention. Preferably, freeze drying is used, and thus the active substances of *H. erinaceus* mycelia in powder form are the freeze-dried powder of the mycelia.

The Effect of the Active Substances on the Body Weight and the Organic Development of the Experimental Animals The model-specific experimental mice were used to simulate senescence at the physiological conditions, and the model-specific mice were proved by the experiment to represent the physiological characteristics of hearing deterioration after feeding for a specific time period. The model-specific experimental mice were grouped randomly, fed on a diet with or without the active substances of *H. erinaceus* mycelia successively for a specific experimental period.

The body weight and the intake of the experimental mice were recorded during the experimental period, and the body weight variation and the intake variation of the experimental mice in each group were calculated after the experiment, so as to determine whether being fed on the diet with the active substances of *H. erinaceus* mycelia has influence on the body weight or the intake of the experimental mice. Finally, the experimental mice were dissected and analyzed to determine the weight of the mice's organs, and the differences between the groups were calculated to determine whether feeding the diet with the active substances of *H. erinaceus* mycelia has any influence on the mice's organs.

The Prevention Effect of the Active Substances on the Hearing Deterioration

Before and after the feeding experiment, auditory brainstem response (ABR) was used to determine the mice's response to the voice stimulation, so as to calculate the hearing threshold. The hearing threshold shift before and after the feeding experiment was the level of hearing deterioration. Furthermore, the difference of the level of hearing deterioration between the groups was compared to investigate the prevention effect of being fed the diet with the active substances of *H. erinaceus* mycelia on hearing deterioration.

The principle of the ABR is to evoke potentials. After stimulation of peripheral nerves, the potential variations in the brain were recorded by the electrode attached to the scalp. The subject's auditory response was tested and analyzed via the waveform diagram to determine the pathology of the auditory nerve or brainstem accordingly. Because this auditory response test method is simply operated and reproducible without being affected by the will and limited by age, the method has been the most widely-used and objective physiological audition test in the past two decades (Starr, A. and Achor, L. J. Arch. Neurol. 1975. 32(11): 761-768.).

Embodiment 1: The Incubation of *H. erinaceus* Mycelia and the Preparation of its Active Substances The incubation on the agar plate:

The *H. erinaceus* mycelium was inoculated on a potato dextrose agar (PDA) plate and incubated at 25° C. for about 7 days.

The incubation in the flask:

The *H. erinaceus* mycelium was aseptically scraped from the agar plate above to inoculate into the medium (see below) in the flask, followed by the shaking incubation in the orbital incubator at a shaking rate of 120 rounds per minute (rpm), at about 26° C., pH 5.0 for 5 days.

The formula of the medium is listed as follows.

| Ingredients | Amount (wt. %) |
| --- | --- |
| Glucose | 2.0 |
| Yeast extract | 0.1 |
| Animal or plant sources of protein and its hydrolyzate | 0.1 |
| Magnesium sulfate | 0.001 |
| Soybean flour | 0.1 |
| Water | Add to 100 wt. % |

The incubation in the fermentation tank:

The medium used in the fermentation tank is the same as the incubation step for the flask. The incubated mycelia in the flask were inoculated into the medium in the fermentation tank. At 26° C., a tank pressure of 0.5-1.0 kg/cm$^2$, pH 5.0 and with or without (mechanical agitation) a stirring rate of 10-150 rpm, the air was introduced at an aeration rate of 0.5-1 volume per volume per minute (vvm), and the inoculated mycelia were incubated for 12 days. The fermented medium containing the mycelia, the supernatant and the active substances of *H. erinaceus* having the prevention effect on hearing deterioration was obtained after 12 days.

Embodiment 2: The Preparation of the Freeze-Dried Powder of *H. erinaceus* Mycelia The fermented medium was freeze-dried to obtain the freeze-dried powder of *H. erinaceus* mycelia. A 20-metric ton fermented medium was freeze-dried to obtain about 80 kg freeze-dried powder.

Embodiment 3: The Experimental Animal Model and the Feeding of the Active Substances of *H. erinaceus* Mycelia The animal model used in the present invention is the senescence-accelerated prone mouse (SAMP8), which belongs to one of the SAMP strains and is considered as an ideal model for investigating age-related deterioration (such as learning, memory and immunodeficiency) and a good model for elucidating the connection between gene regulation and phenotype (Butterfield, D. A. and Poon, H. F. Exp. Gerontol. 2005. 40(10): 774-783.). The mice show senescence-accelerated phenomena at an early stage. The possible reasons may be the increased free radical generation, the decreased antioxidase activity and immunity, the overproduced peroxide and the induced oxidation pressure in vivo. These factors may also be the causes that result in the quick deterioration of the physiological functions.

Before the following experiments, SAMP8 mice's hearing deterioration was determined using the auditory brainstem response. It was found that SAMP8 mice begin to deteriorate after 9-month of age and deteriorate very rapidly after 11-month of age. Therefore, 9-month old SAMP8 strain mice were used as the experimental model in this study to analyze the correlation between the mice and their hearing deterioration symptoms.

The weaned male SAMP8 mice were fed with solid diet (Fwusow Industry, Taiwan) to 9-month age and grouped randomly. The grouped mice lived in the transparent plastic cage with the size of 30 cm (W)×20 cm (D)×10 cm (H), and the cages were stored in the animal house. The temperature and the relative humidity of the animal house were 22±2° C. and 65±5% respectively, and the animal house is an automatic control cleanroom. The light and dark period of the animal house is controlled by the automatic timer with lighting on between 19:00 and 07:00 hours. The basic components of the experimental diet were 20% casein, 5% soybean oil, 1% vitamin mixture (AIN93-VX), 5% mineral mixture (AIN93-G), 2% cellulose powder and 2.5% choline, with the remainder of a mixture of starch and sucrose (2:1).

The mice were divided into three groups: the control group (group A) was fed the diet without the freeze-dried powder of H. erinaceus mycelia, while groups B and C were fed the diet supplemented with different amounts of the freeze-dried powder of H. erinaceus mycelia. Mice in group B were fed with the freeze-dried powder of 215.25 mg/kg body weight/day, and the mice in group C were fed with the freeze-dried powder of 430.5 mg/kg body weight/day. The feeding experiment was performed continuously for 12 weeks.

Embodiment 4: The Effect of Feeding the Active Substances of H. Erinaceus Mycelia to Mice The mice's body weight variation and intake variation were recorded in this experiment during the feeding period, and the differences of the body weight and the daily average intake between groups were analyzed. The experimental results are represented as average±standard error of the mean (S.E.M.), and the statistics were performed using one-way ANOVA. These experimental results are represented in Table 1. It can be known from Table 1 that the body weight gain and the daily average intake between the groups have no significant difference, suggesting that the ingestion of the H. erinaceus freeze-dried powder containing the active substances of H. erinaceus does not influence the mice's intake and does not cause dysplasia in mice.

TABLE 1

The variations of the body weight and the intake of the experimental mice after feeding for 12 weeks

| Group | Number of mice used | Body weight (g) Start | Body weight (g) End | Body weight gain | Intake (g/day) |
|---|---|---|---|---|---|
| A | 8 | 31.41 ± 0.89 | 31.79 ± 1.41 | 0.38 ± 0.66 | 6.46 ± 0.12 |
| B | 8 | 34.93 ± 1.49 | 36.25 ± 1.99 | 1.32 ± 0.64 | 6.69 ± 0.20 |
| C | 8 | 32.26 ± 1.20 | 32.12 ± 1.49 | −0.14 ± 1.02 | 6.78 ± 0.21 |

In addition to the experiments focused on the body weight and intake, the organ weights between the senescence-accelerated prone mice in each group were compared after the 12-week feeding experiment. The experimental results are represented as average±S.E.M., and the statistics were performed using one-way ANOVA. These experimental results are represented in Table 2. It can be known from Table 2 that the average relative weights of heart, liver, spleen, lung, kidney and brain of the mice in each group do not have any significant difference, and no abnormal phenomenon was observed by the naked eye, suggesting that the ingestion of the H. erinaceus freeze-dried powder containing the active substances of H. erinaceus does not have harmful influence on the organs.

TABLE 2

The comparison of the relative weight of the organs in the experimental mice after feeding for 12 weeks

| Group | Number of mice used | Relative weight (g/100 g mouse's body weight) | | | | | |
|---|---|---|---|---|---|---|---|
| | | Heart | Liver | Spleen | Lung | Kidney | Brain |
| A | 8 | 0.53 ± 0.03 | 4.63 ± 0.32 | 0.28 ± 0.01 | 0.85 ± 0.07 | 1.54 ± 0.10 | 1.48 ± 0.06 |
| B | 8 | 0.54 ± 0.05 | 5.53 ± 0.50 | 0.29 ± 0.03 | 0.73 ± 0.03 | 1.57 ± 0.12 | 1.36 ± 0.09 |
| C | 8 | 0.57 ± 0.03 | 4.67 ± 0.24 | 0.29 ± 0.02 | 0.75 ± 0.05 | 1.53 ± 0.05 | 1.47 ± 0.06 |

Embodiment 5: The Prevention Effect of the Active Substances of H. erinaceus Mycelia on the Hearing Deterioration Using Auditory Brainstem Response The auditory brainstem response test was performed before and after the feeding experiment. During the auditory brainstem response test, barbiturate was injected into the experimental mice's peritoneums to anesthetize them, and booster shots of barbiturate were periodically given to the experimental mice to keep them at the adequate anesthetized status. The equipment used in the auditory brainstem response test was the dual-frequency auditory evoked potential system (Intelligent Hearing System, Ronamac International Corp., U.S.A.). The tested site was the left ear, and thus one soft tube was disposed approximately to the left ear to be stimulated by the click sound for 8~10 seconds per stimulation. The test ranges of the stimulation frequency were at low frequency, middle frequency, and high frequency, so that the hearing threshold shifts of the experimental mice at different frequencies were compared. In this experiment, the frequencies for the low-frequency, middle-frequency and high-frequency stimulation sounds were about 2 kHz to 4 kHz (click sound), 8 kHz and 16 kHz, respectively. The response evoked by the stimulation sound was recorded by the software of a multi-functional evoked potential recorder (SmartEP) to obtain the waveform diagram for potential responses which were reproduced by the sound stimulation of different frequencies in the groups. The decibel sound pressure level (Db SPL) for individual stimulation was upregulated or downregulated. According to the waveform diagram for potential responses, the lowest level that the subject could hear the sound was identified to calculate the hearing thresholds before and after the feeding experiment. The calculated values for the click sound, 8-kHz sound and 16-kHz sound represented the hearing thresholds for low frequency, middle frequency and high frequency respectively. The hearing threshold shift was calculated by subtracting the hearing threshold determined at 9-month age from the hearing threshold determined at 12-month age. The results of the hearing threshold shift are shown in Table 3 as follows and represented as average±S.E.M. The statistics were performed using one-way ANOVA, "a" and "b" in superscript refer to the significant differences that exist between the value in one group and that in the other group at a specific frequency when p<0.05. The hearing threshold shifts in Table 3 are further depicted in FIG. 1. It can be known from FIG. 1 that, regardless of the click sound, 8-kHz sound and 16-kHz sound, the hearing threshold shift of the mice (fed the diet without *H. erinaceus* mycelia freeze-dried powder) in Group A (control group) were higher than that of the experimental mice (fed the diet containing different amounts of *H. erinaceus* freeze-dried powder) in Groups B and C, indicating that the range of the hearing deterioration is small in both experimental groups fed with *H. erinaceus* freeze-dried powder, which proves that the active substances of *H. erinaceus* contained in the *H. erinaceus* freeze-dried powder has a prevention effect on hearing deterioration.

TABLE 3

The hearing threshold shift of the experimental mice at different frequencies before and after the feeding experiment

| Group | Number of mice used | Frequency (kHz) | | |
|---|---|---|---|---|
| | | Click | 8 kHz | 16 kHz |
| A | 8 | 11.88 ± 1.32$^a$ | 19.38 ± 3.33$^a$ | 7.50 ± 2.11 |
| B | 8 | 10.00 ± 1.34$^a$ | 10.63 ± 2.20$^b$ | 4.38 ± 1.48 |
| C | 8 | 3.75 ± 1.25$^b$ | 8.75 ± 2.80$^b$ | 5.00 ± 1.64 |

The invention claimed is:

1. A method for decreasing a level of a hearing deterioration in a subject comprising a step of:
    administering to the subject in need of decreasing the level of the hearing deterioration a therapeutically effective amount of a powder of a liquid cultured *Hericium erinaceus* mycelium, wherein the subject has an age-related hearing loss.

2. The method according to claim 1, wherein the powder of the liquid cultured *Hericium erinaceus* mycelium is prepared by a method comprising:
    (a) inoculating an *H. erinaceus* mycelium on an agar plate to be incubated;
    (b) inoculating the incubated mycelium in step (a) into a first medium on a small scale to be incubated;
    (c) inoculating the incubated mycelium in step (b) into a second medium on a large scale to be incubated to obtain a fermented medium; and
    (d) drying the fermented medium in step (c) to obtain the powder of the liquid cultured *Hericium erinaceun* mycelium.

* * * * *